(12) United States Patent
Koltzenburg et al.

(10) Patent No.: US 7,994,227 B2
(45) Date of Patent: *Aug. 9, 2011

(54) NANOPARTICULATE ACTIVE SUBSTANCE FORMULATIONS

(75) Inventors: Sebastian Koltzenburg, Dannstadt-Schauernheim (DE); Stephan Lehmann, Mainz (DE); Bernhard Steinmetz, Rütschenhausen (DE); Wolfgang Schrof, Neuleiningen (DE); Joachim Hadeler, Frankenthal (DE); Winfried Mayer, Bubenheim (DE); Matthias Bratz, Maxdorf (DE); Werner Goedel, Ulm (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1226 days.

This patent is subject to a terminal disclaimer.

(21) Appl. No.: 10/576,921

(22) PCT Filed: Oct. 19, 2004

(86) PCT No.: PCT/EP2004/011797
§ 371 (c)(1),
(2), (4) Date: Jan. 17, 2007

(87) PCT Pub. No.: WO2005/046328
PCT Pub. Date: May 26, 2005

(65) Prior Publication Data
US 2007/0122436 A1 May 31, 2007

(30) Foreign Application Priority Data
Oct. 30, 2003 (DE) .................................. 103 51 004

(51) Int. Cl.
*A61K 47/32* (2006.01)
*A01N 43/00* (2006.01)
*A01N 43/56* (2006.01)

(52) U.S. Cl. .................. 514/772.6; 514/407; 514/772.4; 504/139

(58) Field of Classification Search .................. 514/407, 514/772.4, 772.6; 504/139
See application file for complete search history.

(56) References Cited

U.S. PATENT DOCUMENTS

| 4,409,358 A | 10/1983 | Kraft et al. |
| 4,512,969 A | 4/1985 | Chen |
| 4,528,185 A | 7/1985 | Kraft et al. |
| 5,118,528 A | 6/1992 | Fessi et al. |
| 5,133,908 A | 7/1992 | Stainmesse et al. |
| 5,319,093 A * | 6/1994 | Huth et al. ................. 548/308.7 |
| 5,787,686 A | 8/1998 | Bott et al. |
| 6,458,745 B1 | 10/2002 | Runge et al. |
| 6,616,946 B1 * | 9/2003 | Meier et al. ................... 424/489 |
| 6,869,914 B2 | 3/2005 | Bratz et al. |
| 2003/0118614 A1 | 6/2003 | Sieverding et al. |
| 2005/0032903 A1* | 2/2005 | Suarez-Cervieri et al. ... 514/620 |
| 2005/0101639 A1 | 5/2005 | Ammermann et al. |
| 2005/0165076 A1 | 7/2005 | Ammermann et al. |
| 2005/0182219 A1 | 8/2005 | Meyer et al. |
| 2006/0030486 A1 | 2/2006 | Meyer et al. |
| 2007/0122436 A1 | 5/2007 | Koltzenburg et al. |
| 2008/0287593 A1 | 11/2008 | Oetter et al. |

FOREIGN PATENT DOCUMENTS

| EP | 0 039 788 | 11/1981 |
| EP | 0 275 796 | 7/1988 |
| EP | 0 446 636 | 9/1991 |
| EP | 0 750 899 | 1/1997 |
| EP | 0 875 143 | 11/1998 |
| JP | 2723971 | * 3/1998 |
| WO | WO 97/13503 | 4/1997 |
| WO | WO 98/16105 | 4/1998 |
| WO | WO 01/18064 | 3/2001 |
| WO | WO 02/082900 | 10/2002 |
| WO | WO 03/039249 | 5/2003 |
| WO | WO 03/055944 | 7/2003 |
| WO | WO 03/073851 | 9/2003 |
| WO | WO 03/073852 | 9/2003 |
| WO | WO 2004/000916 | 12/2003 |
| WO | WO 2005/046328 | 5/2005 |

OTHER PUBLICATIONS

U.S. Appl. No. 12/443,921, Koltzenburg et al.
Auweter, H., et al., "Fiber-Optical Quasi-elastic Light Scattering of Concentrated Dispersion", Journal of Colloid and Interface Science, Jun. 1985, pp. 399-409, vol. 105, No. 2.
Lilge, D., et al., "Diffusion in concentrated dispersion: A study with fiber-optic quasi-elastic light scattering (FOQELS)",Colloid & Polymer Science, 1991, pp. 704-712, vol. 269.
Weise, H., et al., "Single-mode fibers in fiber-optic quasielastic light scattering: A study of the dynamics of concentrated latex dispersions", J. Chem. Phys, May 15, 1991, p. 6429-6443, vol. 94, No. 10.

* cited by examiner

*Primary Examiner* — James H Alstrum Acevedo
(74) *Attorney, Agent, or Firm* — Brinks Hofer Gilson & Lione

(57) ABSTRACT

The invention relates to nanoparticulate formulations comprising at least one active compound or compound with a special effect and at least one random radical copolymer. The copolymers are formed from monomers carrying sulfonic acid groups and additional olefinically unsaturated compounds.
The formulations are dispersible as nanoparticles in an aqueous medium. The invention includes, in addition, processes for the preparation of the solid and liquid formulations, and their use.

34 Claims, No Drawings

NANOPARTICULATE ACTIVE SUBSTANCE FORMULATIONS

The present invention relates to active compound formulations which, in addition to at least one active compound, comprise at least one random radical copolymer, which comprises, as monomer units, at least one olefinically unsaturated sulfonic acid i) or a salt thereof or a mixture of acid and salt and at least one alkyl-, aryl-, alkylaryl-, aryl alkyl-, aryloxyalkyl-, alkoxyaryl- or hydroxyalkyl-substituted (meth)acrylate or (meth)acrylamide ii), and if appropriate additional additives.

The invention additionally relates to processes for the preparation of the active compound formulations, dispersions which are prepared by redispersing these active compound formulations in aqueous systems, and the use of these active compound formulations.

Many active compounds are ideally provided in the form of aqueous systems. This naturally makes, more difficult an effective application of active compounds which are insoluble or only slightly soluble in water, since the bioavailability and accordingly the biological activity are low. Many active compounds, especially in the agricultural and pharmaceutical fields, are hydrophobic by nature and therefore are subject to the abovementioned problem of application.

It is known that solubility, dispersibility and bioavailability of active compound particles can be increased by expanding the particle surface area, i.e. by reducing the particle size at an identical total amount. For example, the penetration of biological membranes is simplified at a smaller particle size.

This simultaneously means that, in comparison with the application of the active compound in the form of larger particles, the amounts of active compound necessary to achieve the same effect are smaller when particles in the size range of 1 micrometer and less are used.

Surface active substances, which inhibit crystal growth and agglomeration, are frequently used-to stabilize nanoparticulaite systems. Typical stabilizers are low-molecular-weight surfactants or oligomers which result in the formation of micelles. The active compound content of such micelles is often low, which is disadvantageous. However, high-molecular-weight auxiliaries, such as, for example, colloids, amphiphilic polymers and thickeners, also raise the possibility of stabilizing small active compound particles.

While the abovementioned protective colloids stabilize the particles against agglomeration by covering the surface and leading to repulsive electrostatic and/or steric interactions between the particles, thickeners stabilize kinetically by slowing down the diffusion and accordingly the rate of collision between the particles.

WO 97/13503 reveals a method for of preparation of nanoparticles, in which an agent and a matrix in solution are brought together in order then to be produced in a spray drying step as a nanocomp6site powder which can be redispersed in an aqueous medium. The nanoparticles produced in such a way are smaller than 5000 nm, particularly preferably smaller than 250 nm. In addition to therapeutic and diagnostic agents, inter alia, pesticides are also mentioned as possible applications.

Carbohydrates, proteins, inorganic salts, resins or lipids are mentioned as matrix mate-rials, gelatin, starch, polyvinylpyrrolidone, arabinogalactan, polyvinyl alcohol, poly-acrylic acid, polyethylene, polymethacrylates, polyamide, poly(ethylene-co-vinyl acetate) and shellac being mentioned as resins and celluloses being mentioned as carbohydrates.

Additional components, such as stabilizers and surfactants, have to be added for the redispersing.

EP-A 0 275 796 reveals a process for the preparation of colloidally dispersible systems by the formation of spherical nanoparticles. The process comprises the dissolution of a first component A in a solvent or mixture of solvents, to which surface-active agents are optionally added, and the preparation of a second solvent or mixture of solvents, which second solvent or mixture of solvents does not dissolve the component A. In addition, surface-active agents are optionally added to the second solvent or mixture of solvents and the second solvent/mixture of solvents is miscible in any proportion with the solvent/mixture of solvents of the component A. On mixing the solution of the component with the second solvent/mixture of solvents in a mixing chamber with control of the mixing and residence time (micronizing), nanoparticles with a size of less than 500 nm are formed. Polymers, fats, fatty acid esters, biologically active substances, pigments, lubricants or dyes are mentioned as possible components A.

WO 98/16105 reveals solid plant protection preparations consisting essentially of one or more predominantly amorphous solid per se plant protection active compounds with a solubility in water of less than 500 mg/l at 25° C. and a coating layer surrounding the active compounds. The preparation is produced by mixing a liquid formulation of the plant protection active compound with a liquid formulation of a coating material and drying the plant protection active compound coated in such a way. Preferred solvents are volatile water-miscible solvents. The dried nanoparticles can be redispersed in aqueous media, the particle sizes are 0.1 to 0.8 micrometer. Surface-active polymeric colloids or oligomeric amphiphilic compounds or mixtures thereof are suitable as coating layer materials. Biopolymers and modified biopolymers are preferably used. In addition, synthetic anionic and neutral polymers, for example such as polyvinyl alcohol, polyvinylpyrrolidone and polyacrylic acid, are suitable.

WO 03/039249 refers to a solid plant protection formulation formed from a plant protection agent and a random radical copolymer which comprises at least one hydrophilic and one hydrophobic monomer as polymerized units and optionally additional additives. In the aqueous dispersion described, at least 50% of the dispersed particles are found in a state which is amorphous by X-rays. Procationic nitrogen-comprising compounds, such as vinyl-substituted pyridines or aminoalkyl-substituted (meth)acrylamides, are used as hydrophilic monomers.

EP-A 0 875 143 reveals pesticidal compositions with a polymer content of 0.01 to 40% by weight in which at least one of the components is a polymer which reduces the crystallization of the pesticidal active compound of the composition.

The polymers can have a lipophilic or both a lipo- and hydrophilic character. The hydrophilic character is fixed by monomer units chosen from substituted alkyl esters, alkyl thioesters and mono- or dialkylamides of monoethylenically unsaturated monomers, such as acrylic acid, methacrylic acid, fumaric acid, maleic acid and itaconic acid, substituted or unsubstituted vinyl esters of $C_1$-$C_4$-carboxylates, cyclic esters, amides and heterocycles and vinyl-substituted amines.

The lipophilic character is conferred on the polymers by ethylenically unsaturated monomers, such as long-chain alkyl esters and mono- or disubstituted alkylamides of acrylic acid, methacrylic acid, fumaric acid, maleic acid or itaconic acid, by α-olefins or vinyl alcohol esters, vinyl halides, vinyinitriles and vinyl carboxylates.

WO 02/082900 describes aqueous suspensions of nanoparticles. The nanoparticles are formed from an amphiphilic compound with at least one hydrophobic and at least one hydrophilic unit and at least 50 percent by weight of an organic water-insoluble agrochemical substance based on 100 parts of the amphiphilic compound. Amphiphilic diblock copolymers are revealed as compatibilizers.

DE-A 10151392 describes powdered active compound formulations consisting of a biological active compound, a dispersant, polyvinyl alcohol and if appropriate additives. In this connection, the active compound and the dispersant are suspended in an aqueous phase and heated until molten; an emulsion is formed. This emulsion is homogenized with a jet disperser and is then rapidly cooled until the dispersed melt solidifies. The finely divided dispersion is then treated with an aqueous polyvinyl alcohol solution, whereby a film of polyvinyl alcohol is formed which encloses the particles of the dispersion.

EP-A 0 875 142 reveals dispersions of plant protection active compounds in agricultural oils and a method for the preparation of these dispersions. The size of the dispersed particles is between 0.5 and 10 micrometers. The polymers used to disperse the active compounds consist of from 2.5 to 35% by weight of polar monomers. Monomers carrying hydroxyl, carboxylic acid and nitrogen groups are used as polar monomers. Preferred monomers are long-chain (meth) acrylates and, as polar monomer, dimethylaminopropyl-methacrylamide (DMAPMA).

It was an object of the present invention to provide new possibilities for the formulation of active compounds, in particular for the nanodispersing in an aqueous medium of active compounds which per se have low solubility in water.

The present invention relates to active compound formulations comprising
a. at least one active compound,
b. at least one random radical copolymer comprising, as monomers, at least one olefinically unsaturated sulfonic acid of the formula I

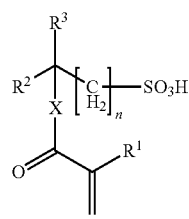

in which X is oxygen or $NR^5 R^1$ is hydrogen or methyl, n can take a value from 0 to 10, $R^2$ and $R^3$ are, independently of one another, $C_1$-$C_6$-alkyl, and $R^5$ is hydrogen, alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl or alkylarylaminoaryl, it being possible for the aryl radicals to be substituted, and where the olefinically unsaturated sulfonic acid can be present in the acid or salt form or as a mixture of the acid and salt forms, at least one olefinically unsaturated monomer of the formula II

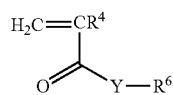

in which Y is oxygen or $NR^5$, $R^4$ is hydrogen or methyl, and $R^5$ and $R^6$ are, independently of one another, hydrogen, alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl or alkylarylaminoaryl, optionally additional monomers, and
c. if appropriate additional additives.

Salts of the sulfonic acid of the formula I are preferably alkali metal or ammonium salts. $C_1$-$C_{20}$-alkyl are suitable as alkyl radicals, alone or in the abovementioned combinations. Mention may in particular be made of $C_1$-$C_6$-alkyl, such as methyl, ethyl, propyl, 1-methylethyl, butyl, 1-methylpropyl, 2-methylpropyl, 1,1-dimethylethyl, pentyl, 1-methyl butyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethyipropyl, 1-ethyl-i-methylpropyl and 1-ethyl-2-methylpropyl, cyclohexyl, n-heptyl, n-octyl, 2-ethylhexyl, decyl, isodecyl, undecyl, lauryl, tridecyl, myristyl, pentadecyl, cetyl, heptadecyl or stearyl.

Aryl radicals is to be understood as meaning mono- or polycyclic, if appropriate substituted, aromatic hydrocarbon radicals. Mention may be made, by way of examples, of phenyl, naphthyl or phenyl substituted by halogen, such as fluorine or chlorine.

Alkoxy is an alkyl radical bonded via an oxygen atom (—O—) to the backbone.

Aryloxy is an aryl radical bonded via an oxygen atom (—O—) to the backbone.

Additional monomers can comprise, for example, vinylaromatic monomers, such as styrene and styrene derivatives, such as α-methylstyrene, vinyltoluene, ortho-, meta- and para-methylstyrene, ethylvinylbenzene, vinyinaphthalene, vinylxylene and the corresponding halogenated vinylaromatic monomers, or vinylaromatic monomers carrying nitro, alkoxy, haloalkyl, alkoxycarbonyl, carboxyl, amino and alkylamino groups, α-olefins, such as ethene, propene, 1-butene, 1-pentene, 1-hexene, isobutene, or α-olefins comprising long-chain ($C_{10}$-$C_{20}$)alkyls, dienes, such as butadiene and isoprene, vinyl alcohol esters, such as vinyl acetate, vinyl halides, such as vinyl chloride, vinyl bromide or vinyl fluoride, vinylidene chloride, vinylidene fluoride, vinylidene bromide, vinylnitrile, vinyl carboxylates, 1-vinylamides, such as 1-vinylpyrrolidone, 1-vinylpiperidone, 1-vinylcaprolactam, 1-vinylformamide, 1-vinylacetamide or 1-methyl-1-vinylacetamide, N-vinylimidazole, $C_1$-$C_{24}$-alkyl esters and mono- and disubstituted and unsubstituted $C_1$-$C_{24}$-alkylamides of monoethylenically unsaturated monomers, such as acrylic acid, methacrylic acid, fumaric acid, maleic acid and itaconic acid, vinylsulfonic acid, anhydrides, such as maleic anhydride, unsaturated aldehydes, such as acrolein, or unsaturated ethers, such as 1,4-cyclohexanedimethanol divinyl ether, 1,4-cyclohexanedimethanol monovinyl ether, butanediol divinyl ether, butanediol monovinyl ether, cyclohexyl vinyl ether, diethylene glycol divinyl ether, ethylene glycol monovinyl ether, ethyl vinyl ether, methyl vinyl ether, n-butyl vinyl ether, octadecyl vinyl ether, triethylene glycol vinyl methyl ether, vinyl isobutyl ether, vinyl (2-ethylhexyl) ether, vinyl propyl ether, vinyl isopropyl ether, vinyl dodecyl ether, vinyl tert-butyl ether, hexanediol divinyl ether, hexanediol monovinyl ether, diethylene glycol monovinyl ether, diethyl-aminoethyl vinyl ether, polytetrahydrofuran-290 divinyl ether, tetraethylene glycol divinyl ether, ethylene glycol butyl vinyl ether, ethylene glycol divinyl ether, triethylene glycol divinyl ether, trimethylolpropane trivinyl ether or aminopropyl vinyl ether.

A polymer described with "radical" is to be understood as meaning a polymer prepared by a radical polymerization.

A copolymer described with "random" is to be understood as meaning a copolymer in which the monomer sequence is determined by the copolymerization parameters of the monomers. This is correspondingly valid also for copolymers consisting of more than two types of monomer.

Polymers of this type are also described as statistical copolymers.

The sulfonic acids of the formula I can be present in the acid or salt form or as a mixture of the acid and salt forms. The term "sulfonic acid" is used for all these forms. Salts of the sulfonic acid are metal salts, in particular alkali metal salts, such as lithium, sodium or potassium salts, or ammonium salts.

In a preferred embodiment, the random radical copolymer according to the invention comprises, as monomers, at least one olefinically unsaturated sulfonic acid of the formula I, at least one (meth)acrylate of the formula IIa

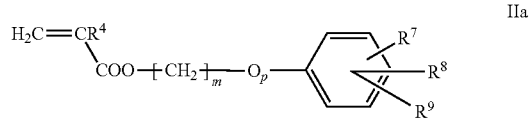

in which m takes the integral values from 0 to 4 and p takes the integral values 0 or 1, $R^4$ is hydrogen or methyl, and $R^7$, $R^8$ and $R^9$ are, independently of one another, hydrogen, $C_1$-$C_6$-alkyl, halogen, hydroxyl or $C_1$-$C_6$-alkoxy, it being possible for alkyl and alkoxy to be halosubstituted, and optionally additional olefinic monomers of the formula IIb

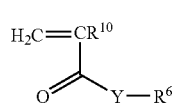

in which Y is O or $NR^5$, $R^{10}$ is hydrogen or methyl, and $R^5$ and $R^6$ are hydrogen, alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl or alkylarylaminoaryl, it being possible for the aryl radicals to be substituted.

In this connection, alkoxy is an alkyl radical as mentioned above which is bonded via an oxygen atom to the backbone. Aryloxy is an aryl radical which is bonded via an oxygen atom (—O—) to the backbone.

Aryl radicals is to be understood as meaning mono- or polycyclic, if appropriate substituted, aromatic hydrocarbon radicals. Mention may be made, by way of examples, of phenyl, naphthyl or phenyl substituted by halogen, such as fluorine or chlorine. Aryloxy is an aryl radical as mentioned above which is bonded via an oxygen atom to the backbone.

By way of example, alkylaryl is tolyl, arylalkyl is benzyl, alkoxyalkyl is ethoxyethyl, aryloxyalkyl is phenoxyethyl, alkoxyaryl is methoxyphenyl, hydroxyalkyl is hydroxyethyl and (di)alkylaminoalkyl is dimethylaminopropyl.

In a particularly preferred embodiment, the random radical copolymer according to the invention is formed from at least one olefinically unsaturated sulfonic acid of the formula I and phenoxy-$C_1$-$C_6$-alkyl acrylate, such as, for example, phenoxyethyl acrylate.

In an additional preferred embodiment, the random radical copolymer is formed from monomers of the above formula I, in particular 2-acrylamido-2-methyl-1-propanesulfonic acid, and at least one olefinically unsaturated monomer of the formula II

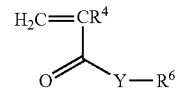

in which Y is oxygen or $NR^5$, $R^4$ is hydrogen or methyl, and $R^5$ and $R^6$ are hydrogen, alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl or alkylarylaminoaryl, in which alkyl and aryl have the abovementioned meanings, and optionally additional monomers.

In an additional particularly preferred embodiment, the random radical copolymer comprises, as monomers, 2-acrylamido-2-methyl-1-propanesulfonic acid and at least one olefinically unsaturated monomer of the formula II, in which Y is oxygen, $R^4$ is hydrogen and $R^6$ is hydrogen or alkyl.

Accordingly, the random radical copolymer comprises, in this particularly preferred embodiment, as monomers, 2-acrylamido-2-methyl-1-propanesulfonic acid and at least one ester of acrylic acid.

Such esters of acrylic acid are, for example, methyl acrylate, ethyl acrylate, propyl acrylate, isopropyl acrylate, butyl acrylate, 2-methylpropyl acrylate, tert-butyl acrylate, hexyl acrylate, cyclohexyl acrylate, n-octyl acrylate, 2-ethylhexyl acrylate, decyl acrylate, isodecyl acrylate, undecyl acrylate, lauryl acrylate, tridecyl acrylate, myristyl acrylate, pentadecyl acrylate, cetyl acrylate, heptadecyl acrylate or stearyl acrylate.

In a very particularly preferred embodiment, the random radical copolymer comprises, as monomers, 2-acrylamido-2-methyl-1-propanesulfonic acid, phenoxyethyl acrylate and at least one ester of acrylic acid.

In an additional very particularly preferred embodiment, the random radical copolymer is formed from the monomers 2-acrylamido-2-methyl-1-propanesulfonic acid and phenoxyethyl acrylate.

The molar weights $M_w$, and $M_n$, and the polydispersity of the polymers, are determined by size exclusion chromatography. Commercial PMMA standard units can be used as calibration material.

According to the invention, the proportion in percent of the at least one olefinically unsaturated sulfonic acid in the total weight of the at least one random radical copolymer is 10 to 90, preferably 20 to 80 and particularly preferably 30 to 70 percent by weight.

The random radical copolymers according to the invention are preferably synthesized in a conventional way by free radical polymerization. However, other, e.g. controlled radical, processes can also be used for the polymerization. The polymerization is carried out in the presence of the monomers and one or more initiators and can be carried out with or without solvent, in emulsion or in suspension.

The polymerization can be carried out as a batch reaction, in a semicontinuous operation or in a continuous operation.

The reaction times generally range between 1 and 12 hours.

The temperature region in which reactions can be carried out generally extends from 20 to 200° C., preferably from 40 to 120° C.

Conventional radical-forming substances are used as initiator for the radical polymerization. The initiator is preferably chosen from the group of the azo compounds, the peroxide compounds or the hydroperoxide compounds. Mention may be made, by way of examples, of acetyl peroxide, benzoyl peroxide, lauroyl peroxide, tert-butyl peroxyisobutyrate, caproyl peroxide, cumene hydroperoxide, azobisisobutyronitrile or 2,2'-azobis(2-methylbutanenitrile). Azobisisobutyronitrile (AIBN) is particularly preferred. The radical polymerization -is preferably carried out in solution. Solvents are water, alcohols, such as, e.g., methanol, ethanol or isopropanol, dipolar aprotic solvents, such as, e.g., DMF, DMSO or NMP, or halogenated or nonhalogenated aromatic or aliphatic hydrocarbons, such as, e.g., hexane, chlorobenzene, toluene or benzene. Preferred solvents are isopropanol, methanol, toluene, DMF, NMP, DMSO and hexane; DMF is particularly. preferred.

According to the invention, the ratio of the proportion by weight of active compound(s) to the proportion by weight of random radical copolymer(s) ranges from 1:10 to 10:1, preferably from 1:4 to 4:1, particularly preferably from 1:2 to 2:1.

Suitable active compounds within the meaning of the present invention are preferably active compounds which are sparingly soluble in water, such as biologically or pharmaceutically active compounds, but also substances with a special effect which are sparingly soluble in water, such as colorants, fragrances, flavorings, and active substances and substances with a special effect used in cosmetics. Sparingly soluble in water means a solubility in water of less than 1000 mg/l, preferably less than 100 mg/l, in each case at a temperature of 20° C.

In the formulations according to the invention, several such active compounds can be present simultaneously.

The invention preferably relates to the formulation of plant protection active compounds, the preparation of these plant protection formulations in dispersed form, and preparations and processes for combating pests and undesirable vegetation by use of the plant protection formulation according to the invention.

Mention may be made, as plant protection active compounds, of fungicides, bactericides, insecticides, acaricides, nematicides, molluscicides, herbicides and plant growth regulators.

Preferred plant protection active compounds are herbicides, acaricides, insecticides, nematicides and fungicides listed under Index of common names. Mention may be made, as examples, of the following herbicides, acaricides, insecticides, nematicides and fungicides:

Abamectin, acephate, acequinocyl, acetamiprid, acethion, acetochlor, acetoprole, acifluorfen, aclonifen, ACN, acrinathrin, acrolein, acrylonitrile, acypetacs, alachlor, alanap, alanycarb, aldicarb, aldimorph, aldoxycarb, aldrin, allethrin, d-trans-allethrin, allidochlor, allosamidin, alloxydim, allyl alcohol, allyxycarb, alorac, alpha-cypermethrin, ametridione, ametryn, ametryne, amibuzin, amicarbazone, amidithion, amidoflumet, amidosulfuron, aminocarb, aminotriazole, amiprofos-methyl, amiton, amitraz, amitrole, ammonium sulfamate, ampropylfos, AMS, anabasine, anilazine, anilofos, anisuron, arprocarb, arsenous oxide, asulam, athidathion, atraton, atrazine, aureofungin, avermectin B1, azaconazole, azadirachtin, azafenidin, azamethiphos, azidithion, azimsulfuron, azinphosethyl, azinphosmethyl, aziprotryn, azithiram, azobenzene, azocyclotin, azothoate, azoxystrobin, barban (=barbanate), barium hexafluorosilicate, barium polysulfide, barium silicofluoride, barthrin, BCPC, beflubutamid, benalaxyl, benazolin, bendiocarb, bendioxide, benefin (=benfluralin), benfuracarb, benfuresate, benodanil, benomyl, benoxafos, benquinox, bensulfuron, bensulide, bensultap, bentaluron, bentazon, benthiocarb, benzadox, benzalkonium chloride, benzamacril, benzamizole, benzamorf, benzene hexachloride, benzfendizone, benzipram, benzobicyclon, benzoepin, benzofenap, benzofluor, benzohydroxamic acid, benzomate benzoximate (=benzoylprop), benzthiazuron, benzyl benzoate, beta-cyfluthrin, beta-cypermethrin, bethoxazin, BHC, gamma-BHC, bialaphos, bifenazate, bifenox, bifenthrin, bilanafos, binapacryl, bioallethrin, bioethanomethrin, biopermethrin, bioresmethrin, biphenyl, bispyribac, bistrifluron, bitertanol, bithionol, blasticidin-S, borax, Bordeaux mixture, BPPS, bromacil, bromchlophos, bromfenvinfos, bromobonil, bromobutide, bromocyclen, bromo-DDT, bromofenoxim, bromomethane, bromophos, bromophos-ethyl, bromopropylate, bromoxynil, brompyrazon, bromuconazole, BRP, bufencarb, bupirimate, buprofezin, Burgundy mixture, butacarb, butachlor, butafenacil, butam, butamifos, butathiofos, butenachlor, buthidazole, buthiobate, buthiuron, butocarboxim, butonate, butoxycarboxim, butralin, butroxydim, buturon, butylamine, butylate, butylchlorophos, cacodylic acid, cadusafos, cafenstrole, caffeine, calcium arsenate, calcium chlorate, calcium cyanamide, calcium polysulfide, cambendichlor, camphechlor, captafol, captan, carbam, carbamorph, carbanolate, carbaryl, carbasulam, carbathion, carbendazim, carbetamide, carbofuran, carbon disulfide, carbon tetrachloride, carbophenothion, carbophos, carbosulfan, carboxazole, carboxin, carfentrazone, carpropamid, cartap, carvone, CDAA, CDEA, CDEC, CEPC, cerenox, cevadilla, Cheshunt mixture, chinalphos, chinalphosmethyl, chinomethionat, chlobenthiazone, chlomethoxyfen, chlor-IPC, chloramben, chloraniformethan, chloranil, chloranocryl, chlorazifop, chlorazine, chlorbenside, chlorbicyclen, chlorbromuron, chlorbufam, chlordane, chlordecone, chlordimeform, chiorethoxyfos, chloreturon, chlorfenac, chlbrfenapyr, chlorfenazole, chlorfenethol, chlorfenidim, chlorfenizon, chlorfenprop, chlorfenson, chlorfensulphide, chlorfenvinphos, chlorfenvinphos-methyl, chlorfluazuron, chlorflurazole, chlorflurecol, chlorflurenol, chloridazon, chlorimuron, chlorinate, chlormephos, chlormethoxynil, chlomitrofen, chloroacetic acid, chlorobenzilate, chloroform, chloromebuform, chloromethiuron, chloroneb, chlorophos, chloropicrin, chloropon, chloropropylate, chlorothalonil, chlorotoluron, chloroxifenidim (=chloroxuron), chloroxynil, chlorphonim, chlorprazophos, chlorprocarb, chlorpropham, chlorpyrifos, chlorpyrifos-methyl, chlorquinox, chlorsulfuron, chlorthal, chlorthiamid, chlorthiophos, chlortoluron, chlozolinate, chromafenozide, cinerin I, cinerin II, cinmethylin, cinosulfuron, cisanilide, cismethrin, clethodim, climbazole, cliodinate, clodinafop, cloethocarb, clofentezine, clofop, clomazone, clomeprop, cloprop, cloproxydim, clopyralid, cloransulam, closantel, clothianidin, clotrimazole, CMA, CMMP, CMP, CMU, copper acetate, copper acetoarsenite, copper arsenate, copper carbonate, basic, copper hydroxide, copper naphthenate, copper oleate, copper oxychloride, copper 8-quinolinolate, copper silicate, copper sulfate, copper sulfate, basic, copper zinc chromate, coumaphos, coumithoate, 4-CPA, 4-CPB, CPMF, 4-CPP, CPPC, cresol (=cresylic acid), crotamiton, crotoxyfos, crufomate, cryolite, cufraneb, cumyluron, cuprobam, cuprous oxide, CVMP, cyanatryn, cyanazine, cyanofenphos, cyanophos, cyanthoate, cyazofamid, cyclafuramid, cyclethrin, cycloate, cycloheximide, cycloprothrin, cyclosulfamuron, cycloxydim, cyflufenamid, cycluron, cyfluthrin, beta-cyfluthrin, cyhalofop, cyhalothrin, gamma-cyhalothrin, lambda-cyhalothrin, cyhexatin, cymoxanil, cypendazole, cypermethrin, alpha-cypermethrin, beta-cypermethrin, theta-cypermethrin, zeta-cypermethrin, cyperquat, cyphenothrin, cyprazine, cyprazole, cyprex, cyproconazole, cyprodinil, cyprofuram, cypromid, cyromazine, cythioate, 2,4-D, 3,4-DA, daimuron, dalapon, dazomet, 2,4-DB, 3,4-DB, DBCP, DCB, DCIP, DCPA (USA), DCPA (Japan), DCU, DDD, DDPP, DDT, pp (pure)-DDT, DDVP, 2,4-DEB, debacarb, decafentin, decarbofuran, dehydroacetic acid, deiquat, delachlor, delnav, deltamethrin, demephion, demephion-O, demephion-S, demeton, demeton-methyl, demeton-O, demeton-O-methyl, demeton-S, demeton-S-methyl, demeton-S-methylsulphon (=demeton-S-methyl sulphone), DEP, 2,4-DEP, depallethrine, derris, 2,4-DES, desmedipham, desmetryn (=desmetryne), diafenthiuron, dialifos, diallate, diamidafos, dianat, diazinon, dibrom, 1,2-dibromoethane, dicamba, dicapthon, dichlobenil, dichlofenthion, dichlofluanid, dichlone, dichloralurea, dichlorfenidim, dichlormate, o-dichlorobenzene, p-dichlorobenzene, 1,2-dichloroethane, dichloromethane, dichlorophen, 1,2-dichloropropane, 1,3-dichloropropene, dichlorprop, dichlorprop-P, dichlorvos, dichlozoline, diclobutrazol, diclocymet, diclofop, diclomezine, dicloran, diclosulam, dicofol, dicresyl, dicrotophos, dicryl, dicyclanil, dieldrin, dienochlor, diethamquat, diethatyl, diethion, diethofencarb, diethyl pyrocarbonate, difenoconazole, difenopenten, difenoxuron, difenzoquat, diflubenzuron, diflufenican (=diflufenicanil), diflufenzopyr, diflumetorim, dilor, dimefox, dimefuron, dimehypo, dimepiperate, dimetan, dimethachlor, dimethametryn, dimethenamid, dimethenamid-P, dimethirimol, dimethoate, dimethomorph, dimethrin, dimethylvinphos, dimetilan, dimexano, dimidazon, dimoxystrobin, dimpylate, dinex, diniconazole, diniconazole-M, dinitramine, dinobuton, dinocap, dinocap-4, dinocap-6, dinocton, dinofenate, dinopenton, dinoprop, dinosam, dinoseb, dinosulfon, dinotefuran, dinoterb, dinoterbon, diofenolan, dioxabenzofos, dioxacarb, dioxathion, diphenamid, diphenyl sulfone, diphenylamine, diphenylsulphide, dipropetryn, dipterex, dipyrithione, diquat, disugran, disul, disulfiram, disulfoton, ditalimfos, dithianon, dithicrofos, dithiometon, dithiopyr, diuron, dixanthogen, DMPA, DNOC, dodemorph, dodicin, dodine, dofenapyn, doguadine, dorametin (=2,4-DP), 3,4-DP, DPC, drazoxolon, DSMA, d-trans-allethrin, dymron, EBEP, ecdysone (=ecdysterone), echlomezol, EDB, EDC, EDDP (=edifenphos), eglinazine, emamectin, EMPC, empenthrin, endosulfan, endothal (=endothall), endothion, endrin, ephirsulfonate, EPN, epofenonane, epoxiconazole, eprinomectin, epronaz, EPTC, erbon, esfenvalerate, ESP, esprocarb, etaconazole, etaphos, etem, ethaboxam, ethalfluralin, ethametsulfuron, ethidimuron, ethiofencarb, ethiolate, ethion, ethiprole, ethirimol, ethoate-methyl, ethofumesate, ethoprop (=ethoprophos), ethoxyfen, ethoxyquin, ethoxysulfuron, ethyl pyrophosphate, ethylan (=ethyl-DDD), ethylene dibromide, ethylene dichloride, ethylene oxide, ethyl formate, ethylmercury acetate, ethylmercury bromide, ethylmercury chloride, ethylmercury phosphate, etinofen, ETM, etnipromid, etobenzanid, etofenprox, etoxazole, etridiazole, etrimfos, EXD, famoxadone, famphur, fenac, fenamidone, fenaminosulf, fenamiphos, fenapanil, fenarimol, fenasulam, fenazaflor, fenazaquin, fenbuconazole, fenbutatin oxide, fenchlorphos, fenethacarb, fenfluthrin, fenfuram, fenhexamid, fenidin, fenitropan, fenitrothion, fenizon, fenobucarb, fenolovo, fenoprop, fenothiocarb, fenoxacrim, fenoxanil, fenoxaprop, fenoxaprop-P, fenoxycarb, fenpiclonil, fenpirithrin, fenpropathrin, fenpropidin, fenpropimorph, fenpyroximate, fenridazon, fenson, fensulfothion, fenteracol, fenthiaprop, fenthion, fenthion-ethyl, fentiaprop, fentin, fentrazamide, fentrifanil, fenuron, fenvalerate, ferbam, ferimzone, ferrous sulfate, fipronil, flamprop, flamprop-M, flazasulfuron, flonicamid, florasulam, fluacrypyrim, fluazifop, fluazifop-P, fluazinam, fluazolate, fluazuron, flubenzimine, flucarbazone, fluchloralin, flucofuron, flucycloxuron, flucythrinate, fludioxonil, fluenetil, flufenacet, flufenerim, flufenican, flufenoxuron, flufenprox, flufenpyr, flumethrin, flumetover, flumetsulam, flumezin, flumiclorac, flumioxazin, flumipropyn, fluometuron, fluorbenside, fluoridamid, fluorochloridone, fluorodifen, fluoroglycofen, fluoroimide, fluoromidine, fluoronitrofen, fluothiuron, fluotrimazole, flupoxam, flupropacil, flupropanate, flupyrsulfuron, fluquinconazole, fluridone, flurochloridone, fluromidine, fluroxypyr, flurtamone, flusilazole, flusulfamide, fluthiacet, flutolanil, flutriafol, fluvalinate, tau-fluvalinate, folpel (=folpet), fomesafen, fonofos, foramsulfuron, formaldehyde, formetanate, formothion, formparanate, fosamine, fosetyl, fosmethilan, fospirate, fosthiazate, fosthietan, fthalide, fuberidazole, furalaxyl, furametpyr, furathiocarb, furcarbanil, furconazole, furconazole-cis, furethrin, furmecyclox, furophanate, furyloxyfen, gamma-BHC, gamma-cyhalothrin, gamma-HCH, glufosinate, glyodin, glyphosate, griseofulvin, guanoctine (=guazatine), halacrinate, halfenprox, halofenozide, halosafen, halosulfuron, haloxydine, haloxyfop, HCA, HCH, gamma-HCH, HEOD, heptachlor, heptenophos, heterophos, hexachlor (=hexachloran), hexachloroacetone, hexachlorobenzene, hexachlorobutadiene, hexaconazole, hexaflumuron, hexafluoramin, hexaflurate, hexazinone, hexylthiofos, hexythiazox, HHDN, hydramethylnon, hydrogen cyanide, hydroprene, hydroxyisoxazole, 8-hydroxyquinoline sulfate, hymexazol, hyquincarb, IBP, imazalil, imazamethabenz, imazamox, imazapic, imazapyr, imazaquin, imazethapyr, imazosulfuron, imiben-conazole, imidacloprid, iminoctadine, imiprothrin, indanofan, indoxacarb, iodobonil, iodofenphos, iodosulfuron, ioxynil, ipazine, IPC, ipconazole, iprobenfos, iprodione, iprovalicarb, iprymidam, IPSP, IPX, isamidofos, isazofos, isobenzan, isocarbamid, ioscil, isodrin, isofenphos, isomethiozin, isonoruron, isopolinate, isoprocarb, isoprocil, iospropalin, isoprothiolane, isoproturon, isothioate, isouron, isovaledione, isoxaben, isoxachlortole, isoxaflutole, isoxapyrifop, isoxathion, isuron, ivermectin, jasmolin I, jasmolin II, jodfenphos, juvenile, hormone I, juvenile, hormone II juvenile, hormone II, karbutilate, kasugamycin, kelevan, kinoprene, kresoxim-methyl, lactofen, lambda-cyhalothrin, lead arsenate, lenacil, leptophos, lime sulfur, d-limonene, lindane, linuron, lirimfos, lufenuron, lythidathion, M-74, M-81, MM, malathion, maldison, malonoben, MAMA, mancopper, mancozeb, maneb, mazidox, MCC, MCPA, MCPA-thioethyl, MCPB, 2,4-MCPB, mebenil, mecarbam, mecarbinzid, mecarphon, mecoprop, mecoprop-P, medinoterb, mefenacet, mefluidide, menazon, MEP, mepanipyrim, mephosfolan, mepronil, mercaptodimethur, mercaptophos, mercaptophos-teolovy, mercaptothion, mercuric chloride, mercuric oxide, mercurous chloride, mesoprazine, mesosulfuron, mesotrione, mesulfen, mesulfenfos, mesulphen, metalaxyl, metalaxyl-M, metam, metamitron, metaphos, metaxon, metazachlor, metazoxolon, metconazole, metflurazon, methabenzthiazuron, methacdfos, methalpropalin, metham, methamidophos, methasulfo-carb, methazole, methfuroxam, methibenzuron, methidathion, methiobencarb, methio-carb, methiuron, methocrotophos, metholcarb, methometon, methomyl, methoprene, methoprotryn, methoprotryne, methoxychlor, 2-methoxyethylmercury chloride, methoxyfenozide, methyl bromide, methylchloroform, methyldithiocarbamic acid, methyldymron, methylene chloride, methyl isothiocyanate, methyl-mercaptophos, methyl-mercaptophos oxide, methyl-mercaptophos-teolovy, methylmercury benzoate, methyl-mercury dicyandiamide, methyl parathion, methyltriazothion, metiram, metobenzuron, metobromuron, metolachlor, S-metolachlor, metolcarb, metominostrobin, metosulam, metoxadiazone, metoxuron, metrafenone, metribuzin, metriphonate, metsulfovax, metsulfuron, mevinphos, mexacarbate, milbemectin, milneb, mipafox, MIPC, mirex, MNAF, molinate, monalide, monisouron, monochloroacetic acid, monocrotophos, monolinuron, monosulfiram, monuron, morfamquat, morphothion, MPMC, MSMA, MTMC, myclobutanil, myclozolin, nabam, naftalofos, naled, naphthalene, naphthalic anhydride, naphthalophos, naproanilide, napropamide, naptalam, natamycin, neburea, neburon, nendrin, nichlorfos, niclofen, niclosamide, nicobifen, nicosulfuron, nicotine, nifluridide, nikkomycins, NIP, nipyraclofen, nitenpyram, nithiazine, nitralin, nitrapyrin, nitrilacarb, nitrofen, nitrofluorfen, nitrostyrene, nitrothalisopropyl, nobormide, norbormide, norea, norflurazon, noruron, novaluron, noviflumuron, NPA, nuarimol, OCH, octhilinone, o-dichlorobenzene, ofurace, omethoate, orbencarb, orthobencarb, orthodichlorobenzene, oryzalin, ovatron, ovex, oxadiargyl, oxadiazon, oxadixyl, oxamyl, oxapyrazon, oxasulfuron, oxaziclomefone, oxine-copper, oxine-Cu, oxpoconazole, oxycarboxin, oxydemeton-methyl, oxydeprofos, oxydisulfoton, oxyfluorfen, oxythioquinox, PAC, pallethrine, PAP, para-dichlorobenzene, parafluron, paraquat, parathion, parathion-methyl, Paris green, PCNB, PCP, p-dichlorobenzene, pebulate, pedinex, pefurazoate, penconazole, pencycuron, pendimethalin, penfluron, penoxsulam, pentachlorophenol, pentanochlor, pentoxazone, perfluidone, permethrin, pethoxamid, PHC, phenetacarbe, phenisopham, phenkapton, phenmedipham, phenmedipham-ethyl, phenobenzuron, phenothiol, phenothrin, phenthoate, phenylmercuriurea, phenylmercury acetate, phenylmercury chloride, phenylmercury nitrate, phenylmercury salicylate, 2-phenylphenol, phorate, phosalone, phosdiphen, phosfolan, phosmet, phosnichlor, phosphamide, phosphamidon, phosphine, phosphocarb, phoxim, phoxim-methyl, phthalide, phthalophos, phthalthrin, picloram, picolinafen, picoxystrobin, piperophos, pirimetaphos, pirimicarb, pirimiphos-ethyl, pirimiphos-methyl, PMA, PMP, polycarbamate, polychlorcamphene, polyethoxyquinoline, polyoxins, polyoxorim, potassium arsenite, potassium cyanate, potassium polysulfide, potassium thiocyanate, prallethrin, precocene I, precocene II, precocene IIII, pretilachlor, primidophos, primisulfuron, probenazole, prochloraz, proclonol, procyazine, procymidone, prodiamine, profenofos, profluazol, profluralin, profoxydim, proglinazine, promacyl, promecarb, prometon, prometryn, prometryne, pronamide, propachlor, propafos, propamocarb, propanil, propaphos, propaquizafop, propargite, propazine, propetamphos, propham, propiconazole, zole, propineb, propisochlor, propoxur, propoxycarbazone, propyzamide, prosulfalin, prosulfocarb, prosulfuron, prothidathion, prothiocarb, prothiofos, prothoate, protrifenbute, proxan, prymidophos, prynachlor, pydanon, pyracarbolid, pyraclofos, pyraclonil, pyraclostrobin, pyraflufen, pyrazolate, pyrazolynate, pyrazon, pyrazophos, pyrazosulfuron, pyrazoxyfen, pyresmethrin, pyrethrin I, pyrethrin II, pyrethrins, pyribenzoxim, pyributicarb, pyriclor, pyridaben, pyridafol, pyridaphenthion, pyridate, pyridinitril, pyrifenox, pyriftalid, pyrimetaphos, pyrimethanil, pyrimicarbe, pyrimidifen, pyrimitate, pyriminobac, pyrimiphos-ethyl, pyrimiphos-methyl, pyriproxyfen, pyrithiobac, pyroquilon, pyroxychlor, pyroxyfur, quassia, quinacetol, quinalphos, quinalphos-methyl, quinazamid, quinclorac, quinconazole, quinmerac, quinociamine, quinomethionate, quinonamid, quinothion, quinoxyfen, quintiofos, quintozene, quizalofop, quizalofop-P, rabenzazole, rafoxanide, reglone, resmethrin, rhodethanil, rimsulfuron, rodethanil, ronnel, rotenone, ryania, sabadilla, salicylanilide, schradan, sebuthylazine, secbumeton, selamectin, sesone, sethoxydim, sevin, siduron, silafluofen, silthiofam, silvex, simazine, simeconazole, simeton, simetryn, simetryne, SMA, sodium arsenite, sodium chlorate, sodium fluoride, sodium hexafluorosilicate, sodium orthophenylphenoxide, sodium pentachlorophenate, sodium pentachlorophenoxide, sodium o-phenylphenoxide, sodium polysulfide, sodium silicofluoride, disodium tetraborate, sodium thiocyanate, solan, sophamide, spinosad, spirodiclofen, spiroxamine, stirofos, streptomycin, sulcofuron, sulcotrione, sulfallate, sulfentrazone, sulfiram, sulfluramid, sulfometuron, sulfosulfuron, sulfotep, sulfotepp, sulfur, sulfuric acid, sulfuryl fluoride, sulglycapin, sulprofos, sultropen, swep, 2,4,5-T, taufluvalinate, tazimcarb, 2,4,5-TB, 2,3,6-TBA, TBTO, TBZ, TCA, TCBA, TCMTB, TCNB, TDE, tebuconazole, tebufenozide, tebufenpyrad, tebupirimfos, tebutam, tebuthiuron, tecloftalam, tecnazene, tecoram, tedion, teflubenzuron, tefluthrin, temephos, TEPP, tepraloxydim, terallethrin, terbacil, terbucarb, terbuchlor, terbufos, terbumeton, terbuthylazine, terbutol, terbutryn, terbutryne, terraclor, tetrachloroethane, tetrachlorvinphos phos, tetraconazole, tetradifon, tetradisul, tetrafluron, tetramethrin, tetranactin, tetrasul, thenylchlor, theta-cypermethrin, thiabendazole, thiacloprid, thiadiazine, thiadifluor, thiamethoxam, thiameturon, thiazafluron, thiazone, thiazopyr, thicrofos, thicyofen, thidiazimin, thidiazuron, thifensulfuron, thifluzamide, thiobencarb, thiocarboxime, fenphim, thiochlorphenphime, thiocyclam, thiodan, thiodicarb, thiofanocarb, thiofanox, thiomersal, thiometon, thionazin, thiophanate, thiophanate-ethyl, thiophanate-methyl, thiophos, thioquinox, thiosultap, thiram, thiuram, thuringiensin, tiabendazole, tiocarbazil tioclorim, tioxymid, TMTD, toiclofosmethyl, tolylfluanid, tolfenpyrad, tolylmercury acetate, toxaphene, 2,4,5-TP, 2,3,3-TPA, TPN, tralkoxydim, tralomethrin, d-trans-allethrin, transfluthrin, transpermethrin, tri-allate, triadimefon, triadimenol, triallate, triamiphos, triarathene, triarimol, triasulfuron, triazamate, triazbutil, triaziflam, triazophos, triazothion, triazoxide, tribenuron, tributyltin oxide, tricamba, trichlamide, trichlorfon trichlormetaphos-3, trichloronat, trichloronate, trichlorphon, triclopyr, tricyclazole, tricyclohexyltin hydroxide, tridemorph, tridiphane, trietazine, trifenofos, trifloxystrobin, trifloxysulfuron, triflumizole, triflumuron, trifluralin, triflusulfuron, trifop, trifopsime, triforine, trimeturon, triphenyltin, triprene, tripropindan, tritac, triticonazole, tritosulfuron, uniconazole, uniconazole-P, validamycin, vamidothion, vaniliprole, vernolate, vinclo-zolin, XMC, xylachlor, xylenols, xylylcarb, zarilamid, zeta-cypermethrin, zinc naphthenate, zineb, zolaprofos, zoxamide trichlorophenate, 1,2-dichloropropane, 1,3-dichloropropene, 2-methoxyethylmercury chloride, 2-phenylphenol, 2,3,3-TPA, 2,3,6-TBA, 2,4-D, 2,4-DB, 2,4-DEB, 2,4-DEP, 2,4-DP, 2,4-MCPB, 2,4,5-T, 2,4,5-TB, 2,4,5-TP, 3,4-DA, 3,4-DB, 3,4-DP, 4-CPA, 4-CPB, 4-CPP, 8-hydroxyquinoline sulfate.

Particularly preferred plant protection active compounds are fungicides, such as, for example:
  acylalanines, such as benalaxyl, metalaxyl, ofurace-or oxadixyl,
  amine derivatives, such as aldimorph, dodine, dodemorph, fenpropimorph, fenpropidin, guazatine, iminoctadine, spiroxamine or tridemorph,
  anilinopyrimidines, such as pyrimethanil, mepanipyrim or cyprodinil,
  antibiotics, such as cycloheximide, griseofulvin, kasugamycin, natamycin, polyoxin or streptomycin,
  azoles, such as bitertanol, bromoconazole, cyproconazole, difenoconazole, diniconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole or triticonazole, dicarboximides, such as iprodione, myclozolin, procymidone or vinclozolin, dithiocarbamates, such as ferbam, nabam, maneb, mancozeb, metam, metiram, propineb, polycarbamate, thiram, ziram or zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine, copper fungicides, such as Bordeaux mixture, copper acetate, copper oxychloride or basic copper sulfate, nitrophenyl derivatives, such as binapacryl, dinocap, dinobuton or nitrothalisopropyl, phenylpyrroles, such as fenpiclonil or fludioxonil, other fungicides, such as acibenzolar-S-methyl, benthiavalicarb, carpropamid, chlorothalonil, cyflufenamid, cymoxanil, dazomet, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide, sulfenic acid derivatives, such as captafol, captan, dichlofluanid, folpet or tolylfluanid, cinnamamides and analogous compounds, such as dimethomorph, flumetover or flumorph.

Very particularly preferred are the strobilurins, such as azoxystrobin, dimoxystrobin, fluoxastrobin, kresoxim-methyl, metominostrobin, orysastrobin, picoxystrobin, pyraclostrobin or trifloxystrobin, in particular pyraclostrobin.

In the formulations according to the invention, several plant protection active compounds—also of a different indication—can be present simultaneously.

A preferred plant protection formulation comprises, as component a), at least one plant protection active compound selected from the class of the fungicides.

Particularly preferred are active compound formulations in which the at least one active compound is selected from the group of the strobilurins; pyraclostrobin is particularly preferred.

Furthermore, particular preference is given to active compound formulations comprising, as active compound, mixtures of pyraclostrobin with additional plant protection active compounds.

Such mixing partners are acylalanines, such as benalaxyl, metalaxyl, ofurace or oxadixyl, amine derivatives, such as aldimorph, dodine, dodemorph, fenpropimorph, fenpropidin, guazatine, iminoctadine, spiroxamine or tridemorph, anilinopyrimidines, such as pyrimethanil, mepanipyrim or cyprodinil, antibiotics, such as cycloheximide, griseofulvin, kasugamycin, natamycin, polyoxin or streptomycin, azoles, such as bitertanol, bromoconazole, cyproconazole, difenoconazole, diniconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole or triticonazole, dicarboximides, such as iprodione, myclozolin, procymidone or vinclozolin, dithiocarbamates, such as ferbam, nabam, maneb, mancozeb, metam, metiram, propineb, polycarbamate, thiram, ziram or zineb, heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine, copper fungicides, such as Bordeaux mixture, copper acetate, copper oxychloride or basic copper sulfate, nitrophenyl derivatives, such as binapacryl, dinocap, dinobuton or nitrothal-isopropyl, phenylpyrroles, such as fenpiclonil or fludioxonil, sulfur, other fungicides, such as acibenzolar-S-methyl, benthiavalicarb, carpropamid, chlorothalonil, cyflufenamid, cymoxanil, dazomet, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene or zoxamide, sulfenic acid derivatives, such as captafol, captan, dichlofluanid, folpet or tolylfluanid, cinnamamides and analogous compounds, such as dimethomorph, flumetover or flumorph.

Preferred mixing partners are metalaxyl, dodemorph, fenpropimorph, fenpropidin, guazatine, spiroxamine, tridemorph, pyrimethanil, cyprodinil, bitertanol, bromoconazole, cyproconazole, difenoconazole, diniconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole, triticonazole, iprodione, vinclozolin, maneb, mancozeb, metiram, thiram, boscalid, carbendazim, carboxin, oxycarboxin, cyazofamid, dithianon, famoxadone, fenamidone, fenarimol, flutolanil, quinoxyfen, thiophanate-methyl, triforine, dinocap, nitrothal-isopropyl, phenylpyrroles, such as fenpiclonil or fludioxonil, acibenzolar-S-methyl, benthiavalicarb, carpropamid, chlorothalonil, cyflufenamid, cymoxanil, fenhexamid, fentin acetate, fenoxanil, fluazinam, fosetyl, fosetyl-aluminum, iprovalicarb, metrafenone, zoxamide, captan, folpet, dimethomorph, azoxystrobin, dimoxystrobin, fluoxastrobin, kresoxim-methyl, metominostrobin, orysastrobin, picoxystrobin or trifloxystrobin.

Particularly preferred mixing partners are metalaxyl, fenpropimorph, fenpropidin, guazatine, spiroxamine, pyrimethanil, cyprodinil, cyproconazole, difenoconazole, epoxiconazole, fenbuconazole, fluquinconazole, flusilazole, hexaconazole, metconazole, myclobutanil, propiconazole, prochloraz, prothioconazole, tebuconazole, triticonazole, iprodione, vinclozolin, boscalid, carbendazim, carboxin, oxycarboxin, cyazofamid, dithianon, quinoxyfen, thiophanate-methyl, dinocap, nitrothal-isopropyl, fenpiclonil or fludioxonil, benthiavalicarb, carpropamid, fenhexamid, fenoxanil, fluazinam, iprovalicarb, metrafenone, zoxamide, dimethomorph, azoxystrobin, dimoxystrobin, fluoxa-strobin, kresoxim-methyl, metominostrobin, orysastrobin, picoxystrobin or trifloxy-strobin.

Very particularly preferred mixing partners are fenpropimorph, cyproconazole, difenoconazole, epoxiconazole, fenbuconazole, fluquinconazole, flusilazole, hexaconazole, metconazole, myclobutanil, propiconazole, prochloraz, prothioconazole, tebuconazole, triticonazole, boscalid, dithianon, quinoxyfen, thiophanate-methyl, dinocap, fenpiclonil or fludioxonil, benthiavalicarb, carpropamid, fenhexamid, fenoxanil, fluazinam, iprovalicarb, metrafenone, zoxamide, dimethomorph, azoxystrobin, dimoxystrobin, fluoxastrobin, kresoxim-methyl, metominostrobin, orysastrobin, picoxystrobin or trifloxy-strobin.

The active compound formulations according to the invention can comprise different amounts and types of additives, such as, for example, solvents.

Thus, solvents can be used, for example, for the preparation of the random radical polymers and of the active compound formulations according to the invention. In an additional embodiment of the invention, the active compound formulations according to the invention can also be present in the form of a fluid solution. Suitable solvents are alcohols, such as, e.g., methanol, ethanol or isopropanol, dipolar aprotic solvents, such as, e.g., DMF, DMSO or NMP, or aromatic, aliphatic, halogenated or nonhalogenated hydrocarbons, such as, e.g., hexane, chlorobenzene, toluene or benzene. Depending on the kind of formulation desired, the solvents can, however, also be removed to the greatest possible extent.

Removed to the greatest possible extent means that the proportion of the solvent remaining in the formulation to the total weight of the formulation is less than 10, preferably bly less than 2 and in particular less than 0.5 percent by weight.

The invention accordingly also relates to active compound formulations in a dried and solid form, i.e. a form freed to the greatest possible extent from the solvent.

The solid active compound formulations can exist in different macroscopic forms. Mention may be made, as examples of macroscopic forms, of spray-dried powder, ground product, granules or film.

The random radical copolymers present in the active compound formulation according to the invention are suitable for dispersing in aqueous systems, in the form of nanoparticulate dispersions, the active compound(s) present in the active compound formulation according to the invention. Such nanoparticulate dispersions comprise at least one continuous phase, which is an aqueous system in the present invention, and at least one dispersed phase. The nanoparticulate dispersions can comprise additional additives.

For this reason, the present invention likewise relates to aqueous dispersions comprising the active compound formulations according to the invention, an aqueous system and if appropriate additional additives.

Such additives are dispersants, thickeners, antifoam agents, bactericides and anti-freeze agents.

Aqueous system is understood as meaning pure water or water comprising a buffer system or salts or additional additives, such as, for example, water-miscible solvents or mixtures thereof.

The pH of the aqueous system generally ranges from 2 to 13, preferably from 3 to 12, particularly preferably from 4 to 10.

The invention also relates to processes for the preparation of aqueous dispersions comprising the active compound formulations according to the invention and optionally additional additives, wherein the active compound formulations according to the invention are brought into contact with an aqueous system and conventionally dispersed.

An important property of the dispersions according to the invention is the mean particle size, determined by quasielastic light scattering, of the dispersed particles, which is, according to the invention, less than 1 micrometer, preferably less than 500 nanometers, particularly preferably less than 100 nanometers. In this connection, particle size is understood as meaning the particle diameter determined by means of quasielastic light scattering. The method of quasielastic light scattering by means of fiber optics is known from the state of the art, for example from H. Auweter, D. Hom, *J. Colloid Interif. Sci.*, 105 (1985), 399, D. Lilge, D. Horn, *Colloid Polym. Sci.*, 269 (1991), 704, or H. Wiese, D. Hom, *J. Chem. Phys.*, 94 (1991), 6429.

Anionic and Nonionic Surfactants Are Used as Dispersants.

Anionic surfactants are alkylarylsulfonates, phenylsulfonates, alkyl sulfates, alkylsulfonates, alkyl ether sulfates, alkylaryl ether sulfates, alkyl polyglycol ether phosphates, polyarylphenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensation products of sulfonated naphthalenes with formaldehyde or with formaldehyde and phenol and if appropriate urea, and condensation products from phenolsulfonic acid, formaldehyde and urea, lignin sulfite waste liquors and lignosulfonates, inclusive of their alkali metal, alkaline earth metal, ammonium and amine salts, alkyl phosphates and polycarboxylates, such as, e.g., polyacrylates, maleic anhydride/olefin copolymers (e.g., Sokalan® CP9, BASF).

Nonionic surfactants, are, for example, alkylphenol alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkylpolyglycosides, glycerol fatty acid esters, polyethylene glycol, polypropylene glycol, polyethylene glycol-/polypropylene glycol block copolymers, polyethylene glycol alkyl ethers, polypropylene glycol alkyl ethers, polyethylene glycol/polypropylene glycol ether block copolymers and their mixtures.

Preferred nonionic surfactants are polyethylene glycol/polypropylene glycol block copolymers, polyethylene glycol alkyl ethers, polypropylene glycol alkyl ethers, polyethylene glycol/polypropylene glycol ether block copolymers and their mixtures.

If appropriate, surfactants are used as additives in the dispersion according to the invention comprising the active compound formulation and an aqueous system. Suitable surfactants are anionic surfactants and nonionic surfactants; mixtures of both are preferred.

The viscosity-modifying additives (thickeners) suitable for the dispersions according to the invention are compounds which confer a pseudoplastic flow behavior on the formulation, i.e. high viscosity at rest and low viscosity in the agitated state. Mention may be made, in this connection, for example, of polysaccharides or organic layered minerals, such as Xanthan Gum® (Keizan® from Kelco), Rhodopol® 23 (Rhône-Poulenc) or Veegum®(R.T. Vanderbilt), or Attaclay® (Engelhardt), XanthanGum® preferably being used.

Silicone emulsions (such as, e.g., Silicone® SRE, Wacker, or Rhodorsil® from Rhodia), long-chain alcohols, fatty acids, fluoroorganic compounds and their mixtures, for example, come into consideration as antifoam agents suitable for the dispersions according to the invention.

Bactericides can be added to stabilize the dispersions according to the invention. Suitable bactericides are, for example, Proxel® from ICI or Acticide® RS from Thor Chemie and Kathon® MK from Röhm & Haas.

Suitable antifreeze agents are, e.g., ethylene glycol, propylene glycerol or glycerol.

If appropriate, the dispersions according to the invention can, to regulate the pH, comprise 1-5% by weight of buffer based on the total amount of the formulation prepared, the amount and type of the buffer used depending on the chemical properties of the active compound or compounds. Examples of buffers are alkali metal salts of weak inorganic or organic acids, such as, e.g., phosphoric acid, boric acid, acetic acid, propionic acid, citric acid, fumaric acid, tartaric acid, oxalic acid and succinic acid.

The invention furthermore relates to processes for the preparation of the active compound formulations according to the invention, which comprise dissolving the at least one active compound and the at least one random radical copolymer, separately from one another, in identical or different organic solvents which are preferably miscible with one another and mixing the solutions thus obtained with one another and optionally adding additives or preparing a combined solution, by presenting the at least one active compound dissolved in an organic solvent and adding the at least one random radical copolymer and optionally additional additives and dissolving, and subsequently removing the solvent or solvents in a conventional way to the greatest possible extent.

Conventional processes for removing solvents are, for example, spray drying, evaporation under reduced pressure, freeze drying, or evaporation at atmospheric pressure and, if appropriate, increased temperature. The processes suitable for drying furthermore include lyophilization or drying in a fluidized bed dryer. The active compound formulations according to the invention are accordingly obtained in a dried form.

If the copolymer necessary for the synthesis is already present in a solvent, this solution is preferably enlisted in the mixing with the active compound or active compound solution.

In a first step, separate solutions of the at least one random radical copolymer and of the at least one active compound in identical or in different solvents are accordingly mixed with one another and additional additives are optionally added. The preparation of a solution of the polymer does not apply if the synthesis of the polymer is carried out in a solvent and this solution is suitable for use in the process for the preparation of the formulation according to the invention.

In this second step, the solvent(s) is/are removed by suitable processes in a conventional way to the greatest possible extent.

The invention furthermore relates to processes for the preparation of the active compound formulation according to the invention, which comprise forrriing an aqueous solution of the at least one random radical copolymer (component b)), dissolving the at least one active compound (component a)) in one or more water-miscible organic solvents, mixing the solutions of the components a) and b) with one another, optionally adding additional additives, obtaining the active compound formulation in dispersed form by introduction of shear forces and subsequently removing the solvents in a conventional way to the greatest possible extent.

Water-miscible means in this connection that the organic solvents are miscible with water without phase separation to at least 10% by weight, preferably to 15% by weight, particularly preferably to 20% by weight.

Should an aqueous solution of the copolymer necessary for this synthesis already exist, this aqueous solution is preferably enlisted in the mixing with the active compound solution.

In a first step, the random radical copolymer(s) and if appropriate additional additives are dissolved in an aqueous system, if such an aqueous solution is not already directly obtained from the step of the polymer synthesis. In addition, the active compound or compounds is/are dissolved in a water-miscible solvent, if appropriate with addition of additional additives.

The two solutions are then mixed with one another.

Provision of energy is advantageous for the preservation of fine particles on mixing the aqueous and organic phases, such as, for example, the application of shear forces, by high-frequency and high-amplitude shaking or high-frequency stirring, turbine agitation, or by use of a mixing chamber.

The mixing can be carried out in a continuous or batchwise fashion Continuous mixing is preferred.

The dispersion obtained in this way can be freed from the solvents in a conventional way as explained above.

Suitable solvents for carrying out the processes for the preparation of a active compound formulation according to the invention are $C_1$-$C_6$-alkyl alcohols, such as methanol, ethanol, propanol, isopropanol, 1-butanol, 2-butanol or tert-butanol, esters, ketones, such as acetone, methyl ethyl ketone, methyl isopropyl ketone or methyl isobutyl ketone, acetals, ethers, cyclic ethers, such as tetrahydrofuran, aliphatic carboxylic acids, such as formic acid, acetic acid or propionic acid, N-substituted or N, N-disubstituted carboxamides, such as acetamide, carboxylates, such as, for example, acetates and lactbnes, such as, for example, butyrolactone, dimethylformamide (DMF) and dimethylpropionamide, aliphatic and aromatic chlorinated hydrocarbons, such as methylene chloride, chloroform, 1,2-,dichloroethane or chlorobenzene, N-lactams, and mixtures of the abovementioned solvents.

Preferred solvents are methanol, ethanol, isopropanol, dimethylformamide, N-methylpyrrolidone, methylene chloride, chloroform, 1,2-dichloroethane, chlorobenzene, acetone, methyl ethyl ketone, methyl isopropyl ketone, methyl isobutyl ketone, tetrahydrofuran, and mixtures of the abovementioned solvents.

Particularly preferred solvents are methanol, ethanol, isopropanol, dimethylformamide and tetrahydrofuran.

Appropriate solids contents of the solutions lie in the concentration range from 0.5 to 30 percent by weight (% by weight), preferably between 1 and 20% by weight.

The active compound formulations according to the invention exist, after removal of the solvent(s), in a dried state.

Naturally, the active compound formulations according to the invention can also exist in the form of suspoemulsions or emulsifiable concentrates with the use of conventional additives and methods known to a person skilled in the art.

The active compound formulations can according to the invention comprise additives. Such suitable additives are known to a person skilled in the art. They can be inert auxiliaries, such as oils of different origins (mineral oils, coal-tar oils, animal and plant oils), aliphatic and aromatic hydrocarbons, such as alkylated naphthalenes, alcohols, such as methanol, ethanol, butanol or cyclohexanol, ketones, such as cyclohexanone, polar solvents and amines, such as N-methylpyrrolidone.

Preferred additives are stabilizers and plasticizers.

Suitable stabilizers can be low-molecular weight components, such as, for example, mono- and diglycerides, esters of the monoglycerides, alkylglucosides, lecithin, fatty acid derivatives of urea and urethanes.

Suitable plasticizers are sucrose, glucose, lactose, fructose, sorbitol, mannitol or glycerol.

The invention additionally relates to active compound formulations comprising pyraclostrobin, wherein the average particle diameter, determined by quasielastic light scattering, is less than 1 micrometer, preferably less than 300 nanometers and particularly preferably less than 100 nanometers.

The following examples illustrate the invention without, however, thereby limiting it:

EXAMPLE 1:

2-Acrylamido-2-methyl-1-propanesulfonic acid-co-phenoxyethyl acrylate-co-n-butyl acrylate (weight ratio 17/33/50)

13.6 g of phenoxyethyl acrylate, 26.4 g of n-butyl acrylate, 40 g of 2-acrylamido-2-methylpropanesulfonic acid and 2.4 g of Wako V60 (azobisisobutyronitrile) were dissolved in 712 g of dimethylformamide (DMF). The vessel was exposed to nitrogen gas and heated to 95° C. After stirring for 4 hours, 0.8 g of Wako V60 in 7.2 g of DMF was added and the mixture was stirred for a further 2 hours.

EXAMPLE 2:

2-Acrylamido-2-methyl-1-propanesulfonic acid-co-n-butyl acrylate (weight ratio 50/50)

40 g of n-butyl acrylate, 40 g of 2-acrylamido-2-methyl-propanesulfonic acid and 2.4 g of Wako V60 (azobisisobutyronitrile) were dissolved in 712 g of DMF. The vessel was exposed to nitrogen gas and heated to 95°F C. After stirring for 4 hours, 0.8 g of Wako V60 in 7.2 g of DMF was added and the mixture was stirred for a further 2 hours.

EXAMPLE 3:

Particle sizes of nanoparticulate dispersions of active compound formulations with different polymers and different polymer/active compound ratios determined using quasielastic light scattering.

Measurements were carried out after 2 hours and after 24 hours.

AMPS: 2-Acrylamido-2-methyl-1-propanesulfonic acid
PEA: Phenoxyethyl acrylate
n-BA n-Butyl acrylate The proportions by weight of the monomers used are indicated, for example, by the numerical sequence 50/17/33, so that AMPS/PEA/n-BA 50/17/33 is to be read as a polymer formed from the monomers 2-acrylamido-2-methyl-1-propanesulfonic acid, phenoxyethyl acrylate and n-butyl acrylate in the weight ratio 50 to 17 to 33.

EXAMPLE 4:

Molar weights of the random radical copolymers

The molar weights of the polymers were determined using size exclusion chromatography. Poly(methyl methacrylate) calibrated test pieces were used as calibration system.

TABLE 2

| Polymer | Number-average $M_n$ | Weight-average $M_w$ | $M_w/M_n$ |
|---|---|---|---|
| AMPS/PEA/n-BA 50/17/33 | 5100 | 22 500 | 4.4 |
| AMPS/n-BA 50/50 | 4800 | 20 000 | 4.2 |

Example 5:

Fungicidal effect of different formulations according to the invention of pyraclostrubin according to the concentration of active compound applied. The character of the damage was determined on wheats of the Kanzler variety which had been infected beforehand with a fungus of the species Puccinia recondite.

The "Active compound formulation" column shows the qualitative and quantitative composition of the respective random radical copolymer present with the active compound in the formulation. The weight ratio of polymer to active compound was 2 to 1 for all formulations.

The "Concentration" column gives the concentration at which the active compound formulation was applied.

The "Rating" column gives, on a scale from 0 to 100, the fungal infection remaining after the treatment, the FIG. 100denoting completely infected. The stated value is a mean value of three individual values.

AMPS: 2-acrylamido-2-methyl-1-propanesulfonic acid
MA, EA, BA, PEA: methyl, ethyl, butyl, phenoxyethyl acrylate

TABLE 3

| Active compound formulation | Concentration [ppm] | Rating (mean value of measurements) |
|---|---|---|
| AMPS/PEA/MA 33/17/50 + Pyraclostrubin | 4 | 0 |
| | 2 | 4 |
| | 1 | 22 |
| | 0.5 | 60 |
| | 0.25 | 67 |

TABLE 1

| Polymer | Active compound | Polymer:Active compound weight ratio | Particle size, 2 hours after preparation of the dispersion (nm) | Particle size, 24 hours after preparation of the dispersion (nm) |
|---|---|---|---|---|
| AMPS/PEA/n-BA 50/17/33 | Pyraclostrubin | 1:1 | 191.9 | 180.7 |
| AMPS/PEA/n-BA 50/17/33 | Pyraclostrubin | 0.5:1 | 125.8 | 136.3 |
| AMPS/PEA/n-BA 50/17/33 | Pyraclostrubin | 0.25:1 | 124.3 | 146.6 |
| AMPS/n-BA 50/50 | Pyraclostrubin | 1:1 | 150.3 | 141.7 |
| AMPS/n-BA 50/50 | Pyraclostrubin | 0.5:1 | 98.7 | 105.1 |
| AMPS/n-BA 50/50 | Pyraclostrubin | 0.25:1 | 124.1 | 130.4 |

TABLE 3-continued

| Active compound formulation | Concentration [ppm] | Rating (mean value of measurements) |
|---|---|---|
| AMPS/PEA/EA 33/50/17 + Pyraclostrubin | 4 | 1 |
| | 2 | 6 |
| | 1 | 17 |
| | 0.5 | 50 |
| | 0.25 | 80 |
| AMPS/PEA 50/50 + Pyraclostrubin | 4 | 1 |
| | 2 | 3 |
| | 1 | 27 |
| | 0.5 | 67 |
| | 0.25 | 77 |
| AMPS/PEA/BA 50/17/33 + Pyraclostrubin | 4 | 6 |
| | 2 | 18 |
| | 1 | 37 |
| | 0.5 | 70 |
| | 0.25 | 80 |
| AMPS/BA 50/50 + Pyraclostrubin | 4 | 0 |
| | 2 | 8 |
| | 1 | 33 |
| | 0.5 | 35 |
| | 0.25 | 73 |

We claim:

1. An active compound formulation comprising
   a) at least one active compound chosen from the group of plant protective active compounds
   b) at least one random radical copolymer formed from the monomers i), ii) and optionally additional monomers, in which i) is at least one olefinically unsaturated sulfonic acid of the formula I

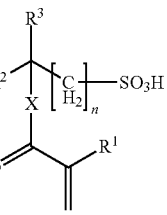

in which
n is 0 or 10
x is O or $NR^5$
$R^1$ is hydrogen or methyl
$R^2$, $R^3$ are, independently of one another, hydrogen or $C_1$-$C_6$-alkyl
$R^5$ is hydrogen, alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl, or alkylarylaminoaryl, it being possible for the aryl radicals to be substituted,
or salts thereof or mixtures of acid and salts, and
ii) is at least one olefinically unsaturated monomer of the formula II

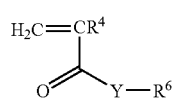

in which
Y is O or $NR^5$,
$R^4$ is hydrogen or methyl,
$R^5$, $R^6$ are hydrogen, alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl or alkylarylaminoaryl, it being possible for the aryl radicals to be substituted,
   in which at least one olefinically unsaturated monomer ii) corresponds to the formula IIb,

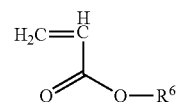

in which $R^6$ is alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl or alkylarylaminoaryl, it being possible for the aryl radicals to be substituted, and
   c) optionally additional additives,
wherein the active compound has a solubility in water of less than 1000 mg/L at a temperature of 20°C.

2. The active compound formulation according to claim 1, wherein the at least one random radical copolymer is formed from
   i) at least one olefinically unsaturated sulfonic acid of the formula I according to claim 24 or salts thereof or mixtures of acid and salts,
   ii) phenoxyethyl acrylate,
   iii) optionally additional olefinically unsaturated monomers of the formula IIb

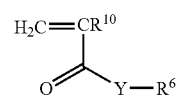

in which
Y is O or $NR^5$,
$R^{10}$ is hydrogen or methyl,
$R^5$, $R^6$ are hydrogen, alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl or alkylarylaminoaryl, it being possible for the aryl radicals to be substituted.

3. The active compound formulation according to claim 1, wherein the monomer i) is 2-acrylamido-2-methyl-1-propanesulfonic acid or a salt thereof or a mixture of acid and salt thereof.

4. The active compound formulation according to claim 1, wherein the at least one random radical copolymer is formed from
i) 2-acrylamido-2-methyl-1-propanesulfonic acid or salts thereof or a mixture of acid and salt thereof
ii) phenoxyethyl acrylate
iii) at least one olefinically unsaturated monomer of the formula IIc $$H_2C=CR^{10}-C(=O)-O-Y-R^6 \quad \text{IIc}$$

in which Y is O
R$^{10}$ is hydrogen or methyl,
R$^6$ are hydrogen, alkyl, aryl, alkylaryl, arylalkyl, alkoxyalkyl, aryloxyalkyl, alkoxyaryl, hydroxyalkyl, (di)alkylaminoalkyl, (di)alkylaminoaryl, (di)arylaminoalkyl, alkylarylaminoalkyl or alkylarylaminoaryl, it being possible for the aryl radicals to be substituted.

5. The active compound formulation according to claim 1, wherein the at least one random radical copolymer is formed from
i) 2-acrylamido-2-methyl-1-propanesulfonic acid or salts thereof or a mixture of acid and salt, and
ii) phenoxyethyl acrylate.

6. The active compound formulation according to claim 1, wherein the proportion of the sulfonic acid or of a salt or of a mixture of acid and salt in the total weight of the copolymer is 10 to 90 percent by weight.

7. The active compound formulation according to claim 1, wherein the proportion of the sulfonic acid or of a salt thereof or of a mixture of acid and salt in the total weight of the copolymer is 30 to 70 percent by weight.

8. The active compound formulation according to claim 1, wherein the ratio of the proportion by weight of component a) to the proportion by weight of component b) ranges from 1:10 to 10:1.

9. The active compound formulation according to claim 1, wherein the ratio of the proportion by weight of component a) to the proportion by weight of component b) ranges from 1:4 to 4:1.

10. The active compound formulation according to claim 1, wherein the ratio of the proportion by weight of component a) to the proportion by weight of component b) ranges from 1:2 to 2:1.

11. The active compound formulation according to claim 1, wherein the at least one active compound is chosen from the group of strobilurins.

12. The active compound formulation according to claim 11, wherein the at least one active compound is pyraclostrobin.

13. The active compound formulation according to claim 1, in solid form.

14. The active compound formulation according to claim 1, in the form of a fluid solution comprising, if appropriate, additional additives.

15. The active compound formulation according to claim 1, in the form of an aqueous dispersion comprising, if appropriate, additional additives.

16. The active compound formulation according to claim 15, wherein the average particle diameter, determined by quasielastic light scattering, is less than 1 micrometer.

17. The active compound formulation according to claim 16, wherein the average particle diameter, determined by quasielastic light scattering, is less than 300 nanometers.

18. The active compound formulation according to claim 17, wherein the average particle diameter, determined by quasielastic light scattering, is less than 100 nanometers.

19. An active compound formulation comprising pyraclostrobin obtained by a process for the preparation of aqueous dispersions which process comprises bringing the active compound formulation according to claim 1, wherein the at least one active compound is pyraclostrobin, if appropriate with addition of one or more additives, into contact with an aqueous system and conventionally dispersing, wherein the average particle diameter, determined by quasielastic light scattering, is less than 1 micrometer.

20. The active compound formulation of claim 19 wherein the average particle diameter, determined by quasielastic light scattering, is less than 300 nanometers.

21. The active compound formulation of claim 19 wherein the average particle diameter, determined by quasielastic light scattering, is less than 100 nanometers.

22. An active compound formulation comprising pyraclostrobin obtained by a process for the preparation of an active compound formulation according to claim 1, wherein the at least one active compound is pyraclostrobin, which process comprises dissolving the components a) and b) and if appropriate c), and optionally additional additives, separately from one another, in identical or different organic solvents and mixing the solutions with one another or preparing a combined solution of the components a) and b) and if appropriate c), and optionally additional additives, by presenting one of the components dissolved in an organic solvent, adding the additional components and dissolving, and optionally subsequently removing the solvent in the greatest possible extent, wherein the average particle diameter, determined by quasielastic light scattering, is less than 1 micrometer.

23. The active compound formulation of claim 22 wherein the average particle diameter, determined by quasielastic light scattering, is less than 300 nanometers.

24. The active compound formulation of claim 22 wherein the average particle diameter, determined by quasielastic light scattering, is less than 100 nanometers.

25. An active compound formulation comprising pyraclostrobin obtained by a process for the preparation of an active compound formulation according to claim 1, wherein the at least one active compound is pyraclostrobin, which process comprises forming an aqueous solution of the component b), and optionally additional additives, dissolving the components a) and, if appropriate, c), and optionally additional additives, in one or more water-miscible organic solvents, mixing the solutions of the components with one another and obtaining the active compound formulation in dispersed form by introduction of energy, and optionally subsequently removing the solvents to the greatest possible extent, wherein the average particle diameter of the active compound, determined by quasielastic light scattering, is less than 1 micrometer.

26. The active compound formulation of claim 25 wherein the average particle diameter, determined by quasielastic light scattering, is less than 300 nanometers.

27. The active compound formulation of claim 25 wherein the average particle diameter, determined by quasielastic light scattering, is less than 100 nanometers.

28. A process for the preparation of aqueous dispersions, which comprises bringing an active compound formulation of claim 1 and optionally one or more additives, into contact with an aqueous system and dispersing.

29. The process according to claim 28 wherein the at least one active compound is pyraclostrobin.

30. A process for the preparation of an active compound formulation of claim 1 comprising dissolving the components a) and b) and if appropriate c), and optionally additional additives, separately from one another, in identical or different organic solvents and mixing the solutions with one another or preparing a combined solution of the components a) and b) and if appropriate c), and optionally additional additives, by presenting one of the components dissolved in an organic solvent, adding the additional components and dissolving, and optionally subsequently removing the solvent to the greatest possible extent.

31. The process according to claim 30 wherein the at least one active compound is pyraclostrobin.

32. A process for the preparation of an active compound formulation of claim 1 comprising forming an aqueous solution of the component b), and optionally additional additives, dissolving the components a) and, if appropriate, c), and optionally additional additives, in one or more water-miscible organic solvents, mixing the solutions of the components with one another and obtaining the active compound formulation in dispersed form by introduction of energy, and optionally subsequently removing the solvents to the greatest possible extent.

33. The process according to claim 32 wherein the at least one active compound is pyraclostrobin.

34. A process for combating harmful fungi, which comprises treating the harmful fungi, their habitat or the plants, surfaces, materials or spaces to be kept free therefrom with an effective amount of a formulation according to claim 1 wherein the at least one active compound is fungicide.

* * * * *

UNITED STATES PATENT AND TRADEMARK OFFICE
CERTIFICATE OF CORRECTION

| | |
|---|---|
| PATENT NO. | : 7,994,227 B2 |
| APPLICATION NO. | : 10/576921 |
| DATED | : August 9, 2011 |
| INVENTOR(S) | : Sebastian Koltzenburg et al. |

Page 1 of 1

It is certified that error appears in the above-identified patent and that said Letters Patent is hereby corrected as shown below:

Col. 21, line 27, delete "protective" and insert therefore --protection--.

Col. 23, line 19, delete "are" and insert therefore --is--; and
line 66, after "diameter" insert --of the active compound--.

Col. 24, line 2, after "diameter" insert --of the active compound--;
line 5, after "diameter" insert --of the active compound--;
line 15, after "diameter" insert --of the active compound--;
line 18, after "diameter" insert --of the active compound--;
line 22, after "diameter" insert --of the active compound--;
line 36, delete "in" and insert therefore --to--;
line 37, after "diameter" insert --of the active compound--;
line 41, after "diameter" insert --of the active compound--; and
line 44, after "diameter" insert --of the active compound--.

Signed and Sealed this
Tenth Day of July, 2012

David J. Kappos
*Director of the United States Patent and Trademark Office*